(12) United States Patent
Nicholas et al.

(10) Patent No.: US 8,704,028 B2
(45) Date of Patent: *Apr. 22, 2014

(54) CONVERSION OF ACYCLIC SYMMETRICAL OLEFINS TO HIGHER AND LOWER CARBON NUMBER OLEFIN PRODUCTS

(75) Inventors: Christopher P. Nicholas, Evanston, IL (US); Etienne Mazoyer, Lyons (FR); Mostafa Taoufik, Villeurbanne (FR); Jean-Marie Basset, Caluire (FR); Paul T. Barger, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 480 days.

This patent is subject to a terminal disclaimer.

(21) Appl. No.: 12/750,005

(22) Filed: Mar. 30, 2010

(65) Prior Publication Data

US 2011/0245569 A1    Oct. 6, 2011

(51) Int. Cl.
*C07C 6/04*      (2006.01)

(52) U.S. Cl.
USPC .......................................... 585/646; 585/643

(58) Field of Classification Search
USPC ................................ 502/323; 585/643, 646
See application file for complete search history.

(56) References Cited

U.S. PATENT DOCUMENTS

| | | | | |
|---|---|---|---|---|
| 3,658,929 A | * | 4/1972 | Banks | 585/324 |
| 3,691,095 A | * | 9/1972 | Kroll et al. | 502/102 |
| 3,978,150 A | | 8/1976 | McWilliams, Jr. | |
| 4,288,688 A | | 9/1981 | Kiyama et al. | |
| 5,026,935 A | | 6/1991 | Leyshon et al. | |
| 5,026,936 A | | 6/1991 | Leyshon et al. | |
| 5,914,433 A | | 6/1999 | Marker | |
| 6,271,430 B2 | * | 8/2001 | Schwab et al. | 585/644 |
| 6,586,649 B1 | | 7/2003 | Botha et al. | |
| 6,646,172 B1 | * | 11/2003 | Schwab et al. | 585/324 |
| 6,777,582 B2 | * | 8/2004 | Gartside et al. | 585/324 |
| 6,858,133 B2 | | 2/2005 | Dath et al. | |
| 6,867,341 B1 | | 3/2005 | Abrevaya et al. | |
| 7,087,155 B1 | | 8/2006 | Dath et al. | |
| 7,214,841 B2 | * | 5/2007 | Gartside et al. | 585/324 |

(Continued)

FOREIGN PATENT DOCUMENTS

| | | |
|---|---|---|
| AU | 2007291786 A1 | 3/2008 |
| CN | 1277608 C | 10/2006 |

(Continued)

OTHER PUBLICATIONS

Taoufik, et al., "Direct Transformation of Ethylene into Propylene Catalyzed by as Tungsten Hydride Supported on Alumina: Trifunctional Single-Site Catalysis" in Angew. Chem. Int. Ed., 2007, 46, 7202-7205—2007, month unknown.*

(Continued)

*Primary Examiner* — In Suk Bullock
*Assistant Examiner* — Bradley Etherton
(74) *Attorney, Agent, or Firm* — Mark Goldberg

(57) ABSTRACT

Processes for the conversion, under conditions and with a catalyst system effective for olefin metathesis, of hydrocarbon feedstocks comprising an acyclic symmetrical olefin (e.g., butene-2) are described. Olefin products of lower and higher carbon numbers (e.g., propylene and pentene) are formed in the presence of a catalyst comprising a solid support and a tungsten hydride bonded to alumina present in the support. This occurs despite the olefin metathesis reaction mechanism leading to a degenerative result, without any expected production of different carbon number products from acyclic symmetrical olefins.

20 Claims, 2 Drawing Sheets

(56) References Cited

U.S. PATENT DOCUMENTS

| | | | |
|---|---|---|---|
| 7,220,886 | B2 | 5/2007 | Podrebarac et al. |
| 7,268,265 | B1 | 9/2007 | Stewart et al. |
| 7,375,257 | B2 | 5/2008 | Dath et al. |
| 7,586,018 | B2 | 9/2009 | Bozzano et al. |
| 7,635,794 | B2 | 12/2009 | Basset et al. |
| 7,638,672 | B2 | 12/2009 | Coperet et al. |
| 2008/0255328 | A1* | 10/2008 | Basset et al. ............ 526/154 |

FOREIGN PATENT DOCUMENTS

| | | |
|---|---|---|
| CN | 101172925 A | 5/2008 |
| EP | 936206 A1 | 10/2002 |
| EP | 1024123 B1 | 4/2004 |
| EP | 1831135 A2 | 9/2007 |
| EP | 2019814 A1 | 2/2009 |
| JP | 11217340 A | 8/1999 |
| WO | 2008001040 A1 | 1/2008 |
| WO | 2008071949 A1 | 6/2008 |
| WO | 2008153643 A1 | 12/2008 |

OTHER PUBLICATIONS

Leofanti, et al., "Surface Area and Pore Texture of Catalysts" in Catalysis Today, 41, 1998, 207-219—1998, month unknown.*

Delaude, et al., "Metathesis" in Kirk-Othmer Encyclopedia of Chemical Technology, John Wiley & Sons, 2001, published on-line Dec. 2, 2005.*

Amigues et al., "Propylene from ethylene and 2-butene," Chinese Petroleum Corp., Hydrocarbon Processing. (ISSN 0018-8190) 69(10) Section1: 79-80 Gulf Publishing (Oct. 1990).

Huang et al., "Metathesis of ethene and 2-butene to propene on W/Al2O3-HY catalysts with different HY contents," Journal of Molecular Cataylsis A; Chemical. 226(1): 61-68 Elsevier (2005).

Search Report dated Feb. 4, 2014 for corresponding Japanese Appl. No. 2013-502692, Nicholas et al.

* cited by examiner

CONVERSION OF ACYCLIC SYMMETRICAL OLEFINS TO HIGHER AND LOWER CARBON NUMBER OLEFIN PRODUCTS

FIELD OF THE INVENTION

The invention relates to processes for the conversion of an acyclic symmetrical olefin (e.g., butene-2) to olefin products of lower and higher carbon numbers (e.g., propylene and pentene) under conditions and in the presence of a catalyst for olefin metathesis. A representative catalyst comprises a tungsten hydride bonded to alumina that is present in a support.

DESCRIPTION OF RELATED ART

Propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. Currently, the majority of propylene is produced during the steam cracking or pyrolysis of hydrocarbon feedstocks such as natural gas, petroleum liquids, and carbonaceous materials (e.g., coal, recycled plastics, and organic materials). The major product of steam cracking, however, is generally ethylene and not propylene.

Steam cracking involves a very complex combination of reaction and gas recovery systems. Feedstock is charged to a thermal cracking zone in the presence of steam at effective conditions to produce a pyrolysis reactor effluent gas mixture. The mixture is then stabilized and separated into purified components through a sequence of cryogenic and conventional fractionation steps. Generally, the product ethylene is recovered as a low boiling fraction, such as an overhead stream, from an ethylene/ethane splitter column requiring a large number of theoretical stages due to the similar relative volatilities of the ethylene and ethane being separated. Ethylene and propylene yields from steam cracking and other processes may be improved using known methods for the metathesis or disproportionation of $C_4$ and heavier olefins, in combination with a cracking step in the presence of a zeolitic catalyst, as described, for example, in U.S. Pat. Nos. 5,026,935 and 5,026,936. The cracking of olefins in hydrocarbon feedstocks, to produce these lighter olefins from $C_4$ mixtures obtained in refineries and steam cracking units, is described in U.S. Pat. Nos. 6,858,133; 7,087,155; and 7,375,257.

Steam cracking, whether or not combined with conventional metathesis and/or olefin cracking steps, does not yield sufficient propylene to satisfy worldwide demand. Other significant sources of propylene are therefore required. These sources include byproducts of fluid catalytic cracking (FCC) and resid fluid catalytic cracking (RFCC), normally targeting gasoline production. FCC is described, for example, in U.S. Pat. No. 4,288,688 and elsewhere. A mixed, olefinic $C_3/C_4$ byproduct stream of FCC may be purified in propylene to polymer grade specifications by the separation of $C_4$ hydrocarbons, propane, ethane, and other compounds.

Much of the current propylene production is therefore not "on purpose," but as a byproduct of ethylene and gasoline production. This leads to difficulties in coupling propylene production capacity with its demand in the marketplace. Moreover, much of the new steam cracking capacity will be based on using ethane as a feedstock, which typically produces only ethylene as a final product. Although some hydrocarbons heavier than ethylene are present, they are generally not produced in quantities sufficient to allow for their recovery in an economical manner. In view of the current high growth rate of propylene demand, this reduced quantity of co-produced propylene from steam cracking will only serve to accelerate the increase in propylene demand and value in the marketplace.

A dedicated route to light olefins including propylene is paraffin dehydrogenation, as described in U.S. Pat. No. 3,978,150 and elsewhere. However, the significant capital cost of a propane dehydrogenation plant is normally justified only in cases of large-scale propylene production units (e.g., typically 250,000 metric tons per year or more). The substantial supply of propane feedstock required to maintain this capacity is typically available from propane-rich liquefied petroleum gas (LPG) streams from gas plant sources. Other processes for the targeted production of light olefins involve high severity catalytic cracking of naphtha and other hydrocarbon fractions. A catalytic naphtha cracking process of commercial importance is described in U.S. Pat. No. 6,867,341.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such processes may be improved using olefin cracking to convert some or all of the $C_4^+$ product of MTO in an olefin cracking reactor, as described in U.S. Pat. No. 7,268,265. An oxygenate to light olefins conversion process in which the yield of propylene is increased through the use of dimerization of ethylene and metathesis of ethylene and butylene, both products of the conversion process, is described in U.S. Pat. No. 7,586,018.

Despite the use of various dedicated and non-dedicated routes for generating light olefins industrially, the demand for propylene continues to outpace the capacity of such conventional processes. Moreover, further demand growth for propylene is expected. A need therefore exists for cost-effective methods that can increase propylene yields from both existing refinery hydrocarbons based on crude oil as well as non-petroleum derived feed sources.

SUMMARY OF THE INVENTION

The invention is associated with processes for the production of olefin products such as propylene, from olefins in a hydrocarbon feedstock having a different carbon number. More particularly, it has been surprisingly determined that an acyclic symmetrical olefin (e.g., butene-2) can be converted to olefin products of lower and higher carbon numbers using a particular olefin metathesis catalyst system. According to present understanding, the olefin metathesis reaction results in redistribution of alkylidene radicals that would be generated upon cleavage of the carbon-carbon double bond of an acyclic olefin. For example, in the case of self-metathesis, the reaction of a single olefin reactant with itself results in rearrangement of the olefinic carbon atom substituents according to the following reaction:

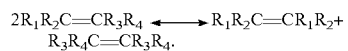

This reaction is described, for example, in US 2008/0255328, where $R_1$-$R_4$ represent hydrogen or hydrocarbon radicals, each of which is bonded to a carbon atom of the olefinic carbon-carbon double bond. Therefore, the self-metathesis of an asymmetrical olefin such as propylene ($R_1$, $R_2$, and R$_3$ are all —H and R$_4$ is —CH$_3$), produces both a lower carbon number olefin (e.g., ethylene) and a higher carbon number olefin (e.g., butene-2), as confirmed in working examples of US 2008/0255328, utilizing an alumina supported tungsten hydride catalyst. However, in the metathesis of a symmetrical olefin, meaning the R$_1$ and R$_2$ groups are the same as R$_3$ and R$_4$ without regard to the cis and trans configuration (i.e., R$_1$=R$_3$ and R$_2$=R$_4$ or R$_1$=R$_4$ and R$_2$=R$_3$), a degenerative result is expected, as the two alkylidene fragments, generated from cleavage of the carbon-carbon double bond, are identical. This expectation is experimentally verified, for example, in the reaction of ethylene to produce ethylene, the reaction of butene-2 to produce butene-2, the reaction of hexene-3 to produce hexene-3, etc., as obtained in conventional olefin metathesis catalyst and reaction systems. Given the art-recognized understanding that the metathesis of acyclic symmetrical olefins is degenerative, one would not expect a metathesis catalyst system to effectively produce new products from the conversion of acyclic symmetrical olefins of the formula

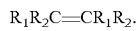

The tungsten hydride/alumina catalyst described in US 2008/0255328 for olefin metathesis was also previously shown to be effective in alkane metathesis in US 2007/129584. According to this publication, the metathesis of an alkane using the tungsten hydride/alumina catalyst, to produce the next higher and lower carbon number homologues, provides a high selectivity for the normal (unbranched) hydrocarbons.

The art therefore recognizes that (i) the tungsten hydride/alumina catalyst system is effective in paraffin and olefin metathesis, and (ii) the metathesis of acyclic olefins having the same substituents on each of the olefinic carbon atoms (i.e., "acyclic symmetrical olefins" for purposes of the present disclosure) does not appreciably form higher and/or lower carbon number products. Surprisingly, however, experimental results now directly contradict expectations based on this knowledge. In particular, it has been discovered that hydrocarbon feedstocks comprising predominantly (e.g., greater than 50% by weight of) one or more acyclic symmetrical olefins can be contacted with a particular type of catalyst having a known olefin metathesis function, under olefin metathesis conditions, to produce appreciable quantities of olefin products of differing carbon numbers (e.g., first and second olefin products having lower and higher carbon numbers relative to the acyclic symmetrical olefin(s)). The catalyst found to unexpectedly provide this result comprises a solid support and a tungsten hydride bonded to alumina present in the support.

With respect to the particular acyclic symmetrical olefin, butene-2, the resulting lower carbon number product is propylene. Representative processes according to the invention can therefore advantageously produce propylene from a single carbon number olefin (e.g., a 4 carbon number olefin), rather than relying on the cross-metathesis of olefins of differing carbon numbers, as in the case of the reaction between ethylene and butylene to produce propylene. This provides a number of commercial advantages over conventional propylene production methods via olefin metathesis, including eliminating the need for sources of different feedstock components at the same location. For example, ethylene is typically obtained as a product of steam cracking, and in particular is recovered as a low boiling fraction from an ethylene/ethane splitter. Butylene, on the other hand, may be obtained from crude oil refining operations or non-petroleum based processes. While sources of both ethylene and butylene may be present at a given location, this is not necessarily the case. Moreover, butylene is generally a less expensive feedstock component than ethylene, meaning that the overall economics of propylene production from butylene may be considerably improved, compared to those of conventional olefin metathesis processes involving reaction between ethylene and butylene.

Accordingly, embodiments of the invention relate to processes for producing olefins, comprising contacting a hydrocarbon feedstock with a catalyst comprising a solid support and a tungsten hydride bonded to alumina present in the support. The feedstock comprises an acyclic symmetrical olefin, and contacting of the feedstock with the catalyst produces first and second olefin products, respectively, having lower and higher carbon numbers relative to the acyclic symmetrical olefin. In representative embodiments, the acyclic symmetrical olefin is present in an amount of at least 80% by weight of the total olefins in the hydrocarbon feedstock.

As discussed above, more particular embodiments of the invention relate to processes for producing propylene, comprising contacting a hydrocarbon feedstock comprising predominantly butene-2 with a catalyst comprising a solid support and a tungsten hydride bonded to alumina present in the support. A per pass conversion of butene-2 according to this embodiment is from about 15% to about 50% by weight, and the butene-2 is converted to propylene with a selectivity of at least about 45% by weight. According to any of the above embodiments, the catalyst may comprise tungsten in an amount from about 1% to about 10% by weight and the support may have a surface area surface area from about 100 m$^2$/g to about 450 m$^2$/g.

These and other aspects and embodiments associated with the present invention are apparent from the following Detailed Description.

Figure 1:
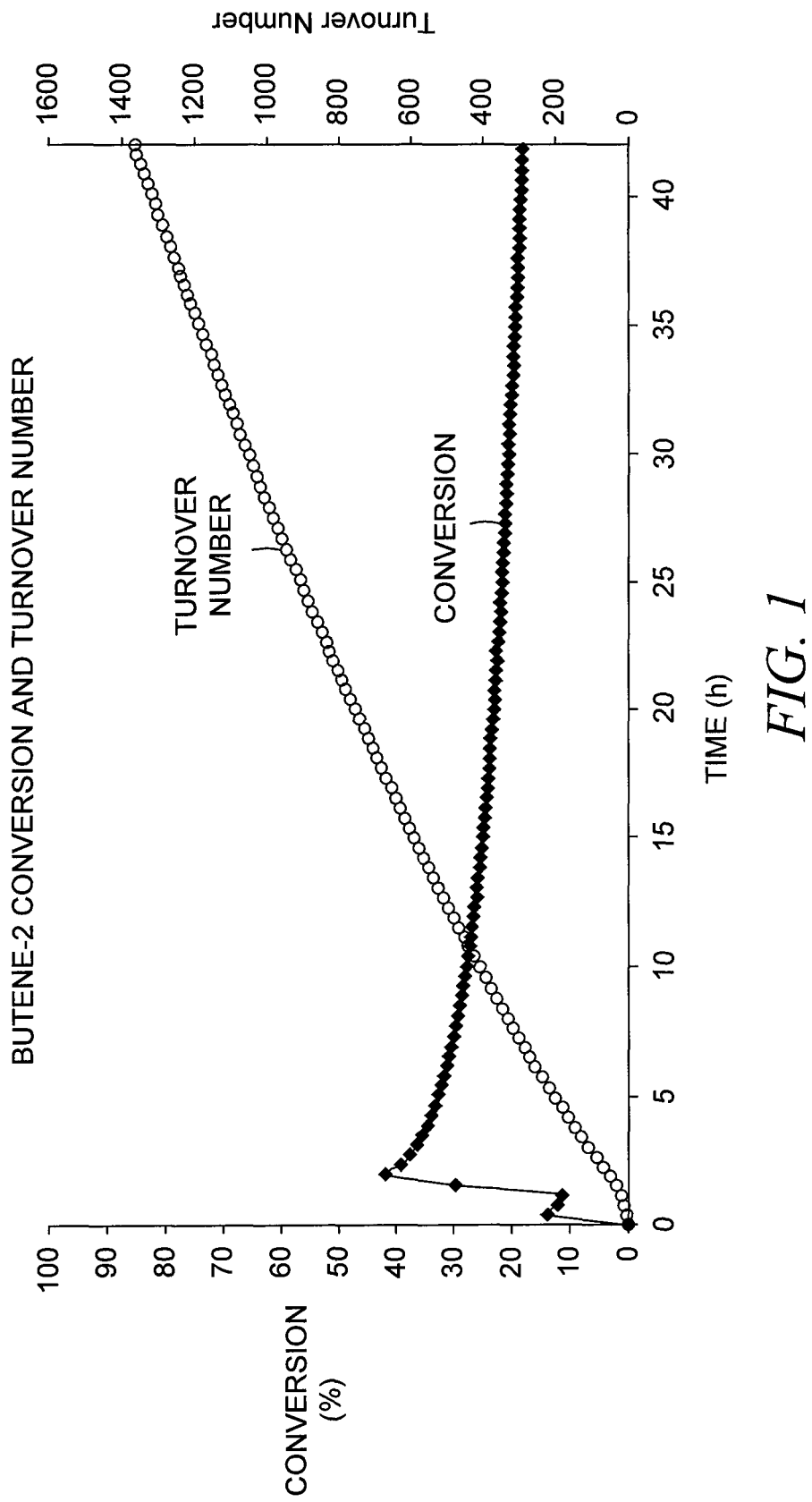
FIG. 1 is a graph showing the (i) conversion of butene-2 and (ii) turnover number (i.e., total moles of butene-2 converted per mole of tungsten metal in the catalyst) as a function of time on stream. The conversion data were obtained in the production of propylene from butene-2.
Figure 2:
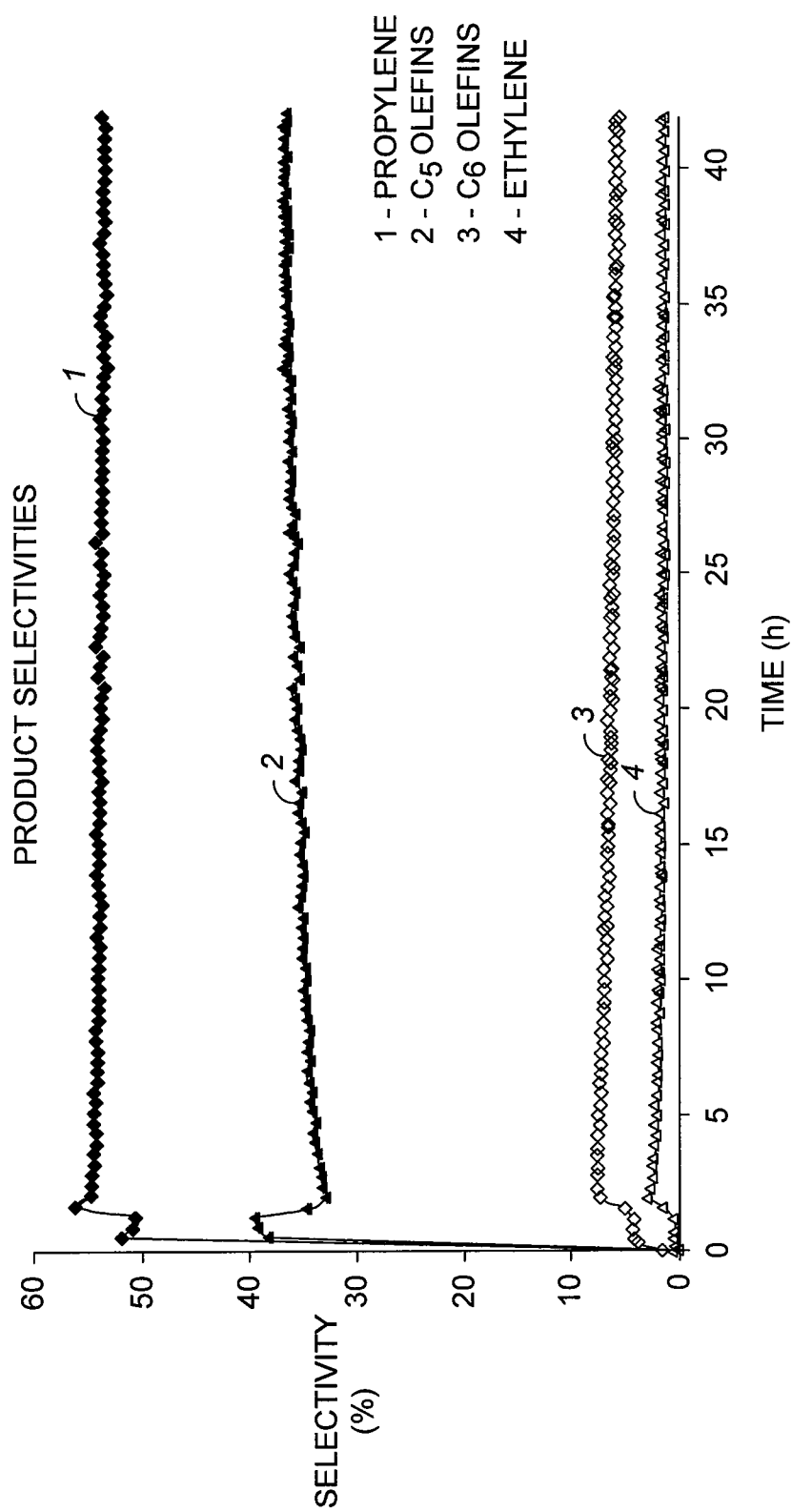
FIG. 2 is a graph showing the selectivities of the main products, propylene and pentene (all C$_5$ olefins), as well as the ethylene and hexene (all C$_6$ olefins), as a function of time on stream. The selectivity data were obtained in the same experiment used to obtain the conversion and turnover data shown in FIG. 1.

The catalyst used to obtain the data presented in FIGS. 1 and 2 was a catalyst comprising a tungsten hydride bonded to alumina present in the support.

DETAILED DESCRIPTION

As discussed above, the present invention is associated with catalyst systems for olefin metathesis (or disproportionation) processes in which a hydrocarbon feedstock is contacted, in a metathesis reactor or reaction zone. Importantly, it has now been discovered that such catalyst systems, in which a tungsten hydride is bonded to alumina present in the catalyst support, effectively convert hydrocarbon feedstocks comprising acyclic symmetrical olefins to desired products of different carbon numbers (i.e., olefin products having lower and higher carbon numbers relative to the acyclic symmetrical olefin).

The acyclic symmetrical olefin refers generally to a compound having an olefinic, carbon-carbon double bond that (i)

is not part of a ring structure and (ii) has the same carbon atom substituents on each carbon atom of the carbon-carbon double bond, regardless of the cis or trans orientation of these substituents. Splitting of the carbon-carbon double bond therefore results in identical alkylidene radicals. For example, compounds of the formula $R_1R_2C\!=\!CR_2R_1$ are necessarily acyclic symmetrical olefins for purposes of this disclosure, whether the $R_1$ and $R_2$ substituents are in a cis or a trans relationship, as illustrated below

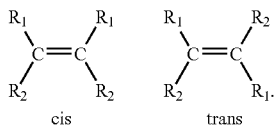

The substituents $R_1$ and $R_2$ of the representative acyclic symmetrical olefins shown above may be independently a hydrogen radical or a hydrocarbon radical, resulting from the removal of one or two hydrogen atoms from a terminal carbon atom of a straight-chain, branched chain, or cyclic (e.g., cycloparaffinic or aromatic) hydrocarbon, optionally having one or more carbon-carbon double bonds and/or one or more carbon-carbon triple bonds. In the case of a hydrocarbon radical, therefore, the terminal carbon atom has a site for a single bond or a double bond between the hydrocarbon radical and a carbon atom of the olefinic carbon-carbon double bond. If the site is for a single bond, then the carbon atom will have two substituents ($R_1$ and $R_2$), whereas if the site is for a double bond, then carbon atom will have only one substituent (e.g., the single substituent will be $R_1$, and $R_2$ will be nonexistent). According to other embodiments, $R_1$ and/or $R_2$ may be a radical in which one or more carbon atoms the hydrocarbon radicals described above may independently be (i) optionally substituted with a straight-chain, branched chain, or cyclic hydrocarbon radical (ii) optionally substituted with a heteroatomic group such as —OH, —SH, —SOH, —SO$_2$H, —SO$_3$H, —NH$_2$, —NO$_2$, —CO$_2$H, —CONH$_2$, —CN, —F, —Cl, —Br, —I, =O, =S, =NH, =NOH, or =NNH$_2$, and/or (iii) optionally replaced by a divalent heteroatomic group such as —O—, —S—, —SO—, —SO$_2$—, or —NH—. Often, $R_1$ and $R_2$ will be independently a hydrogen radical or an alkyl radical (e.g., methyl, ethyl, propyl, etc.), and preferably an alkyl radical having from 1 to 6 carbon atoms. Exemplary acyclic symmetrical olefins are therefore butene-2 ($R_1$=—H and $R_2$=—CH$_3$) and hexene-3 ($R_1$=—H and $R_2$=—C$_2$H$_5$), with butene-2 being preferred.

The acyclic symmetrical olefin is further characterized in that it can produce both higher and lower carbon number olefins. It will be appreciated that ethylene is not included, as there is no olefin having a lower carbon number.

The hydrocarbon feedstock, comprising an acyclic symmetrical olefin as discussed above, refers to the total, combined feed, including any recycle hydrocarbon streams, to a reactor or reaction zone having a catalyst as described herein and under reaction conditions including those that are normally effective for olefin metathesis. The hydrocarbon feedstock does not include any non-hydrocarbon gaseous diluents (e.g., nitrogen), which may be added according to some embodiments. The hydrocarbon feedstock may, but does not necessarily, comprise only hydrocarbons. The hydrocarbon feedstock generally comprises predominantly (i.e., at least 50% by weight) hydrocarbons, typically comprises at least about 80% (e.g., from about 80% to about 100%) hydrocarbons, and often comprises at least about 90% (e.g., from about 90% to about 100% by weight) hydrocarbons.

Also, in processes according to the present invention, the hydrocarbons contained in the hydrocarbon feedstock are generally predominantly (i.e., at least 50% by weight, such as from about 60% to about 100% by weight) olefins (e.g., structural and positional isomers) having the same carbon number of the as the acyclic symmetrical olefin. In the case of butene-2, for example, this acyclic symmetrical olefin, in addition to butene-1 and isobutylene, may in combination represent predominantly the total hydrocarbons of the hydrocarbon feedstock. In more particular embodiments, olefins having the same carbon number as the acyclic symmetrical olefin are present in an amount of at least about 75% (e.g., from about 75% to about 100%) by weight, and often in an amount of at least about 85% (e.g., from about 85% to about 100% or from about 95% to about 100%) by weight, based on the total hydrocarbons of the hydrocarbon feedstock. In other embodiments, the above percentage ranges of olefins having the same carbon number as the acyclic symmetrical olefin are representative of their contribution to the total olefins present in the hydrocarbon feedstock. In still other embodiments, the above percentage ranges of olefins having the same carbon number as the acyclic symmetrical olefin are representative of their contribution to the total hydrocarbon feedstock, rather than their contribution to the total hydrocarbons or the total olefins present in the hydrocarbon feedstock.

In yet further embodiments, the above percentage ranges, namely at least 50% (e.g., from about 60% to about 100%) by weight, at least about 75% (e.g., from about 75% to about 100%) by weight, and at least about 85% (e.g., from about 85% to about 100% or from about 95% to about 100%) by weight, are representative of the percentage of the acyclic symmetrical olefin (e.g., butene-2) with respect to (i) the total hydrocarbons in the hydrocarbon feedstock, (ii) the total olefins in the hydrocarbon feedstock, or (iii) the total hydrocarbon feedstock. In still further embodiments, the hydrocarbon feedstock may comprise all or substantially all acyclic symmetrical olefin. That is, the acyclic symmetrical olefin may be present in the hydrocarbon feedstock in an amount of at least about 90% (e.g., from about 95% to about 100%) by weight.

To achieve a sufficient concentration of the acyclic symmetrical olefin in the hydrocarbon feedstock (or in a hydrocarbon feedstock component that is combined with a recycle stream, as discussed below, to provide the hydrocarbon feedstock), it may be necessary to purify this olefin reactant from other olefins of the same carbon number, namely the structural and positional isomers as discussed above. For example, in many cases the acyclic symmetrical olefin of interest is present in refinery or non-petroleum based process streams as a mixture that is at or near equilibrium with these other isomers. It may be advantageous to use such a mixture as the hydrocarbon feedstock (or combine such a mixture, as a hydrocarbon feedstock component, with a recycle stream, as discussed below, to provide the hydrocarbon feedstock), without separation or purification of any desired isomer(s). Separation of the acyclic symmetrical olefin, upstream of the reactor or reaction zone, to a purity substantially in excess of its equilibrium concentration may be achieved using known techniques including distillation and adsorptive separation (including moving bed and simulated moving bed systems known in the art). In any such separation, generally a stream rich in isomers other than the acyclic symmetrical olefin (i.e., containing any one or more of these other isomers in a concentration in excess of equilibrium) is also produced. Subjecting this stream to isomerization to restore equilibrium or near equilibrium levels of isomers can then generate an additional amount of the acyclic symmetrical olefin for contacting with the tungsten hydride/alumina catalyst, as described herein. For example, suitable isomerization catalysts and processes for increasing the content of the acyclic symmetrical olefin, butene-2, in a mixture of butenes having a sub-equilibrium concentration of this acyclic symmetrical olefin are known in the art and include, for example, magnesium oxide containing isomerization catalysts as described in U.S. Pat. No. 4,217,244.

Integrated processes according to aspects of the invention therefore include separating, using a separation process (e.g., distillation or adsorptive separation), the acyclic symmetrical olefin (e.g., butene-2) from an impure mixture of this olefin with other olefin isomers of the same carbon number to provide an acyclic symmetrical olefin-rich stream (i.e., having a concentration of the acyclic symmetrical olefin above its equilibrium concentration with the other olefin isomers) and an acyclic symmetrical olefin-lean stream (i.e., having a concentration of the acyclic symmetrical olefin below its equilibrium concentration with the other olefin isomers). The hydrocarbon feedstock that is contacted with the tungsten hydride/alumina catalyst, according to this embodiment, comprises at least a portion of the acyclic symmetrical olefin-rich stream. Optionally, the acyclic symmetrical olefin-lean stream is then isomerized to provide an isomerization product comprising an additional amount of the acyclic symmetrical olefin, and this isomerization product may be recycled to the separation process to which the impure mixture, described above, is also fed.

In other embodiments, it may be desirable to increase the butene-2 content in the hydrocarbon feedstock by subjecting an impure mixture of this olefin with other olefin isomers of the same carbon number (e.g., in the case where the impure mixture is an acyclic symmetrical olefin-lean stream, having a concentration of the acyclic symmetrical olefin below its equilibrium concentration with the other olefin isomers) to isomerization to convert, for example, butene-1 and isobutylene to additional butene-2. The isomerization may be performed in a reactor or reaction zone that is separate from (e.g., immediately upstream of) the reactor or reaction zone containing the tungsten hydride/alumina catalyst. Alternatively, the isomerization may be performed in the same reactor that contains this catalyst, for example by incorporating an isomerization catalyst upstream of the tungsten hydride/alumina catalyst or even by combining the two catalysts in a single catalyst bed.

Aspects of the present invention are therefore directed to the production of at least first and second olefin products from an acyclic symmetrical olefin as described above. The first and second olefin products, respectively, have lower and higher carbon numbers relative to the acyclic symmetrical olefin reactant. In an exemplary embodiment, the acyclic symmetrical olefin reactant is butene-2 (having four carbons) and the first and second olefin products are propylene (having two carbons) and pentene (having five carbons). The term "pentene" is meant to encompass all of the various structural and positional isomers of the $C_5$ olefins, including pentene-2, pentene-2,2-methyl butene-1,3-methyl butene-1,2-methyl butene-2,3-methyl butene-2, etc.

The acyclic symmetrical olefin may be derived from petroleum or non-petroleum sources. Crude oil refining operations yielding olefins, and particularly butylene (as a mixture of the $C_4$ olefins butene-1, butene-2, and isobutylene), include hydrocarbon cracking processes carried out in the substantial absence of hydrogen, such as fluid catalytic cracking (FCC) and resid catalytic cracking (RCC). Various olefins including butylene are recovered in enriched concentrations from known separations, including fractionation, of the total reactor effluents from these processes. Non-petroleum sources of butylene include products of oxygenate to olefins conversion processes, and particularly methanol to light olefins conversion processes. Such processes are known in the art, as discussed above, and optionally include additional conversion steps to increase the butylene yield such as by dimerization of ethylene and/or selective saturation of butadiene, as described in U.S. Pat. No. 7,568,018. According to particular embodiments of the invention, therefore, at least a portion of the acyclic symmetrical olefin (e.g., butene-2) in the hydrocarbon feedstock is obtained from an oxygenate to olefins conversion process.

In representative olefin production processes, with an exemplary process being the conversion of the acyclic symmetrical olefin butene-2 for the production of the higher value product propylene, catalysts comprising a solid support and a tungsten hydride bonded to alumina present in the support (i.e., the tungsten hydride/alumina catalyst), may be used to achieve economically favorable product yields under commercial process conditions, including process conditions known to be effective for olefin metathesis. The per pass conversion level of the acyclic symmetrical olefin is generally at least about 15% by weight and typically from about 15% to about 50% by weight. The per pass conversion level is based on the per pass conversion of the total amount of olefins in the hydrocarbon feedstock having the same carbon number as the acyclic symmetrical olefin.

In one or more separations (e.g., fractionation) of the reactor or reaction zone effluent downstream of the reactor or reaction zone where the hydrocarbon feedstock is contacted with the tungsten hydride/alumina catalyst, the desired product (e.g., propylene) may be recovered in substantially pure form by removing and recovering (I) unconverted olefins having the same carbon number as the acyclic symmetrical olefin, and (II) other reaction products (e.g., pentenes and $C_6^+$ hydrocarbons including olefin oligomers and alkylbenzenes). Recycling of all or a portion of (I) back to the reactor or reaction zone may often be desirable for achieving complete or substantially complete overall conversion, or at least significantly higher overall conversion (e.g., from about 80% to about 100% by weight, or from about 95% to about 100% by weight) than the per pass conversion levels indicated above. In other embodiments, it may be desirable to further separate (I) into (Ia) the acyclic symmetrical olefins, or an acyclic symmetrical olefin-rich stream and (Ib) an acyclic symmetrical olefin-lean stream, with streams (Ia) and (Ib) having concentrations of the acyclic symmetrical olefin above and below, respectively, its equilibrium concentration with the other olefin isomers. In this case, all or a portion of (Ia) may be recycled directly back to the reaction or reaction zone, while all or a portion of (Ib) may be isomerized, as described above, to provide an isomerization product comprising an additional amount of the acyclic symmetrical olefin, and all or a portion of this isomerization product may be recycled to the reactor or reaction zone or otherwise to a separation process upstream of the reactor or reaction zone, described above, to separate the acyclic symmetrical olefin in a purified form.

Downstream separation(s) of the first and/or second olefin product(s) from the reactor or reaction zone effluent, in addition to those described above, are normally carried out to achieve high purity/purities of the desired product(s), particularly in the case of propylene. For example, the propylene product typically has a purity of at least about 99% by volume, and often at least about 99.5% by volume to meet polymer grade specifications. According to other embodiments, the propylene purity may be lower, depending on the end use of this product. For example, a purity of at least about 95% (e.g., in the range from about 95% to about 99%) by volume may be acceptable for a non-polymer technology such as acrylonitrile production, or otherwise for polypropylene production processes that can accommodate a lower purity propylene.

At the per pass conversion levels discussed above, the selectivity of the converted feedstock olefin components having the same carbon number as the acyclic symmetrical olefin (e.g., butene-2) to the desired olefin(s), and particularly the first olefin product (e.g., propylene) having a lower carbon number is generally at least about 45% (e.g., in the range from about 45% to about 60%) by weight. The selectivity of the second olefin product (e.g., pentene) having a higher carbon number is generally at least about 30% (e.g., in the range from about 30% to about 45%) by weight. The per pass yield of the desired olefin product(s) is the product of the selectivity to this/these olefin product(s) and the per pass conversion, which may be within the ranges discussed above. The overall yield, using separation and recycle of unconverted olefins having the same carbon number as the acyclic symmetrical olefin, as discussed above, can approach this/these product selectivity/selectivities, as essentially complete conversion is obtained (minus some purge and solution losses of the hydrocarbon feedstock and product(s), as well as losses due to downstream separation inefficiencies).

The conversion and selectivity values discussed above are achieved by contacting the hydrocarbon feedstock described above, either continuously or batchwise, with a tungsten hydride/alumina catalyst as described herein, comprising a solid support and a tungsten hydride bonded to alumina present in the support. Generally, the contacting is performed with the hydrocarbon feedstock being passed continuously through a fixed bed of the catalyst in a reactor or reaction zone, normally under conditions effective for olefin metathesis. For example, a swing bed system may be utilized, in which the flowing hydrocarbon feedstock is periodically re-routed to (i) bypass a bed of catalyst that has become spent or deactivated and (ii) contact a bed of fresh catalyst. A number of other suitable systems for carrying out the hydrocarbon feedstock/catalyst contacting are known in the art, with the optimal choice depending on the particular feedstock, rate of catalyst deactivation, and other factors. Such systems include moving bed systems (e.g., counter-current flow systems, radial flow systems, etc.) and fluidized bed systems, any of which may be integrated with continuous catalyst regeneration, as is known in the art.

As discussed above, the use of the tungsten hydride/alumina catalyst system, in combination with catalyst/feedstock contacting conditions generally favorable for olefin metathesis, surprisingly results in the production of lower and higher carbon number olefin products from a feedstock comprising an acyclic symmetrical olefin. Due to the degenerative nature of the olefin metathesis reaction mechanism with acyclic symmetrical olefins, olefin products with other carbon numbers would not be expected in appreciable amounts. This is especially true in the case of hydrocarbon feedstocks comprising all or a large proportion (e.g., from about 80% to about 100% or even from about 90% to about 100%) of the acyclic symmetrical olefin (e.g., butene-2).

Representative conditions for contacting of the hydrocarbon feedstock with the tungsten hydride/alumina catalyst, at which the above conversion and selectivity levels may be obtained, include a temperature from about 75° C. (167° F.) to about 250° C. (482° F.), and often from about 100° C. (212° F.) to about 200° C. (392° F.); an absolute pressure from about 0.1 bar (1.5 psi) to about 100 bar (1450 psi), and often from about 0.5 bar (7.3 psi) to about 35 bar (508 psi); and a weight hourly space velocity (WHSV) from about 1 $hr^{-1}$ to about 100 $hr^{-1}$, and often from about 5 $hr^{-1}$ to about 25 $hr^{-1}$. As is understood in the art, the WHSV is the weight flow of the hydrocarbon feedstock divided by the weight of the catalyst bed and represents the equivalent catalyst bed weights of feed processed every hour. The WHSV is related to the inverse of the reactor residence time. Under the olefin metathesis conditions described above, the hydrocarbon feedstock is normally partially or all in the vapor phase in the olefin metathesis reactor or reaction zone, but it may also be in the liquid phase, for example, in the case of heavier (higher carbon number) olefin feedstocks.

Importantly, the tungsten hydride/alumina catalysts according to embodiments of the invention and providing the significant benefits, as discussed above, comprise a tungsten hydride that is bonded to an oxygen atom of alumina present in the support. In general, the support comprises predominantly (i.e., at least 50% by weight) alumina, with the optional addition of other components such as other inorganic refractory metal oxides (e.g., silica, zirconia, titania, boria, thoria, ceria) and/or catalyst promoters or modifiers (e.g., alkali or alkaline earth metals, or transition metals in addition to tungsten). Typically, the support comprises alumina in an amount of at least about 90% (e.g., from about 90% to about 100%) by weight and often at least about 95% (e.g., from about 95% to about 100%) by weight.

The catalyst therefore comprises a support comprising alumina (aluminum oxide) to which a tungsten hydride is covalently bonded (grafted). The term "a tungsten hydride" refers to a tungsten compound that is supported on the catalyst. The tungsten atom of the tungsten compound is bonded to at least one hydrogen atom or hydrocarbon residue by at least one single, double, or triple bond. The tungsten atom is also bonded, through an oxygen linkage, to an aluminum atom of the alumina support. The tungsten hydride may be identified by one or more absorption bands, under infrared (IR) spectroscopy that are characteristic of a (W—H) bond, as described below. Otherwise, the tungsten hydride (W—H) bond may be detected with proton nuclear magnetic resonance (solid 1H-NMR) at 500 MHz, where the value of the tungsten hydride chemical shift $\delta_{W-H}$ is typically found at a value of about 10.6 parts per million (ppm) (e.g., in the range from about 10.3-10.9 ppm).

In representative supports, the alumina (aluminum oxide) is accessible to the tungsten hydride at the surface of the support. The support may be a relatively homogeneous composition comprising alumina throughout the mass of the support (e.g., from the core to the surface of the support). Alternatively, the support may be a relatively heterogeneous composition comprising alumina that is present, for example, only at a surface layer. In the latter case, the support may comprise aluminum oxide deposited, supported, or grafted onto an inorganic solid which may itself be an inorganic solid support, for example selected from metals, oxides, sulfides, and salts. Exemplary inorganic solids therefore include other inorganic refractory metal oxides besides alumina.

The support has a surface area generally within a range from 0.1 to 1000 $m^2/g$, and often from about 100 $m^2/g$ to about 450 $m^2/g$. Surface area is measured according to the Brunauer, Emmett and Teller (BET) method based on nitrogen adsorption (ASTM D1993-03 (2008)). The support may comprise all or substantially all aluminum oxide, or it may be mixed with other support components, for example with more than 2% by weight of one or more other inorganic refractory metal oxides (e.g., silica). Also, the aluminum oxide of the support may be modified by one or more elements from groups 14 to 17 of the periodic table of the elements. The elements germanium and tin of group 14 are representative. For element group designations described herein, reference is made to the "CRC Handbook of Chemistry and Physics", 76$^{th}$ Edition (1995-1996), by David R. Lide, published by CRC Press, Inc. (USA), in which the groups of the periodic table are numbered 1 to 18.

The alumina of the support may be, for example, a porous alumina, non-porous alumina, a mesoporous alumina, or any mixture of two or all three of these aluminas. Porous aluminas are frequently referred to as "activated aluminas" or alternatively "transition aluminas." Porous aluminas are often partially hydroxylated and obtained by an "activation" treatment comprising heating and dehydration of a precursor selected from aluminum hydroxides (e.g., aluminum tri-hydroxides), hydroxides of aluminum oxide, or gel-form aluminum hydroxides. The activation treatment eliminates water present in the precursor, together with a proportionate amount of the hydroxyl groups, thereby leaving behind some residual hydroxyl groups and a specific porous structure. The surface of porous aluminas generally comprises a complex mixture of aluminum and oxygen atoms, as well as hydroxyl ions, all of which combine according to the specific crystalline form of the alumina and provide both acidic and basic sites. The alumina of the solid support may be a porous alumina selected from Y-alumina (gamma-alumina), η-alumina (eta-alumina), δ-alumina (delta-alumina), θ-alumina (theta alumina), K-alumina (kappa-alumina), ρ-alumina (rho-alumina) and X-alumina (chi-alumina), and preferably from among Y-alumina, δ-alumina, θ-alumina, and their mixtures. These various crystalline forms depend essentially on the selection of the precursor and the conditions of the activation treatment, in particular temperature and pressure. The activation treatment may be performed, for example, under a stream of air or another gas, such as an inert gas, at a temperature which may be within a range generally from 100° C. (212° F.) to 1000° C. (1832° F.), and typically from 200° C. (392° F.) to 1000° C. (1832° F.).

It is also possible to use porous or alternatively semi-porous aluminas, produced by an activation treatment as previously described, in particular comprising heating to a temperature from 500° C. (932° F.) to 1000° C. (1832° F.). These porous or semi-porous aluminas may comprise mixtures of porous aluminas in at least one of the previously described crystalline forms, such as Y-alumina, η-alumina, δ-alumina, θ-alumina, K-alumina, ρ-alumina or X-alumina, with a non-porous alumina (e.g., α-alumina), which may be present in the alumina in widely varying amounts (e.g., from 20% to 80% by weight). Porous aluminas are generally thermal decomposition products of aluminum tri-hydroxides, aluminum oxide hydroxides (or aluminum oxide hydrates), and gel-form aluminum hydroxides (or alumina gels). Aluminum tri-hydroxides of the general formula Al(OH)$_3$=Al$_2$O$_3$.3H$_2$O may exist in various crystalline forms, such as gibbsite or hydrargillite (α-Al(OH)$_3$), bayerite (β-Al(OH)$_3$), or nordstrandite. Aluminum tri-hydroxides may be obtained by precipitation from aluminum salts in generally alkaline solutions. Aluminum oxide hydroxides of the general formula AlO(OH)=Al$_2$O$_3$.H$_2$O may also exist in various crystalline forms, such as diaspore (β-AlO(OH)) or boehmite (or α-AlO(OH)). Diaspore may be found in certain types of clay and bauxite, and may be synthesized by heat treatment of gibbsite at about 150° C. (302° F.) or by hydrothermal treatment of boehmite at about 380° C. (716° F.) under a pressure of about 500 bar (7250 psi). Boehmite may readily be obtained by heating the resultant gel-form precipitate with cold treatment of the aluminum salt solutions with ammonia. Aluminum oxide hydroxides may also be obtained by hydrolysis of aluminum alcoholates.

Gel-form aluminum hydroxides (or alumina gels) are generally aluminum polyhydroxides, in particular of the general formula: nAl(OH)$_3$.(n−1)H$_2$O, in which n is a number ranging from 1 to 8. Gel-form aluminum hydroxides may be obtained by one of the methods selected from among thermal decomposition of an aluminum salt, such as aluminum chloride, electrolysis of an aluminum salt, such as a mixture of aluminum sulfate and an alkali metal sulfate, hydrolysis of an aluminum alcoholate, such as aluminum methylate, precipitation from aluminates, such as an alkali metal or an alkaline-earth metal aluminate, and precipitation from an aluminum salt, for example by contacting an aqueous solution of Al$_2$(SO$_4$)$_3$ and ammonia, or of NaAlO$_2$ and an acid, or of NaAlO$_2$ and Al$_2$(SO$_4$)$_3$, after which the resultant precipitate may undergo aging and drying to remove water. Gel-form aluminum hydroxides generally assume the form of an amorphous alumina gel, and in particular the form of a pseudoboehmite.

Porous aluminas may have a specific surface area (BET) generally in a range from 50 m$^2$/g to 1000 m$^2$/g, typically from 75 m$^2$/g to 600 m$^2$/g, and often from 100 m$^2$/g to 450 m$^2$/g, with a range from 100 m$^2$/g to 250 m$^2$/g being exemplary. They may furthermore have a specific pore volume of generally at most 1 cm$^3$/g, typically at most 0.9 cm$^3$/g, and often at most 0.75 cm$^3$/g.

Non-porous aluminas include α-alumina (alpha-alumina), generally known as "calcined alumina" or "flame alumina" and existing in a natural state known as "corundum." They may in general be synthesized by a heat treatment, and in particular calcination, of a precursor selected from aluminum salts, aluminum oxide hydroxides, aluminum tri-hydroxides, and aluminum oxides, such as Y-alumina, at a temperature of greater than 1000° C. (1832° F.), and often greater than 1100° C. (2012° F.). Non-porous aluminas may contain impurities, such as other oxides, for example Fe$_2$O$_3$, SiO$_2$, TiO$_2$, CaO, Na$_2$O, K$_2$O, MgO, SrO, BaO and Li$_2$O, in proportions of less than 2% by weight, and often less than 1% by weight. They may have a specific surface area (BET) generally in a range from 0.1 m$^2$/g to less than 300 m$^2$/g, typically from 0.5 m$^2$/g to 300 m$^2$/g, and often from 0.5 m$^2$/g to 250 m$^2$/g. The support may also comprise a mesoporous alumina, for example having a surface area (BET) generally in the range of from 100 m$^2$/g to 800 m$^2$/g. Mesoporous aluminas generally have pores of an average width of from 2 nm to 0.05 μm.

As discussed above, the support may also comprise mixed aluminum oxides, or aluminum oxides combined with at least one other oxide in an amount generally from 2% to less than 80% by weight, typically from 2% to less than 50% by weight, and often from 2% to less than 40% by weight, with an amount from 2% to less than 30% by weight being exemplary. The other oxide(s) may be oxides of an element, M, selected from among metals of groups 1 to 13 and elements of group 14, with the exception of carbon, of the periodic table of the elements. More particularly, they may be oxides of an element M selected from alkali metals, alkaline-earth metals, transition metals and elements of groups 13 and 14, with the exception of carbon. Transition metals generally comprise the metals of groups 3 to 11, and often the elements 21 to 29, 39 to 47, 57 to 79 (including lanthanides) and actinides. The other oxide(s) are often oxides of an element M selected from transition metals of groups 3 to 7, lanthanides, actinides, and elements of groups 13 and 14, with the exception of carbon. More particularly, they may be selected from oxides of silicon, boron, gallium, germanium, titanium, zirconium, cerium, vanadium, niobium, tantalum, chromium, molybdenum, and tungsten.

The support may have a homogeneous composition throughout the entire mass of the support, or it may be heterogeneous and comprise, for example an aluminum oxide, mixed aluminum oxide, or modified aluminum oxide, as previously described, in the form of a surface layer of the support having a thickness that is less than a smallest dimension of the support, for example less than the diameter of a spherical support or less than the diameter of the circular cross section of a cylindrical support. In the case of a heterogeneous composition for the support, the core of the support (e.g., the portion that is not the surface layer) may comprise or consist of an inorganic solid selected from a metal, an oxide, a sulfide, and a salt. Inorganic refractory metal oxides are representative. The heterogeneous support may be prepared by dispersion, by precipitation, and/or by grafting of one of the precursors of aluminum oxide, as described above, onto the inorganic solid. Suitable precursors may include aluminum hydroxides, such as aluminum tri-hydroxides, aluminum oxide hydroxides, and gel-form aluminum hydroxides. Gel-form aluminum hydroxides (known as alumina gels or amorphous aluminas), as described previously, are preferred. A heterogeneous support may for example be produced by processing such a precursor by a sol-gel method or with the assistance of an organometallic compound that facilitates grafting onto the inorganic solid.

The catalyst, comprising a solid support comprising alumina, generally has the form of discreet particles of varying shapes and sizes. For example, the particles may have an average size of generally from 10 nm to 5 mm, and often from 20 μm to 4 mm. The particles may assume their natural shape or may be shaped to have any of a number of forms, including a spherical, a spheroidal, a hemispherical, a hemispheroidal, a cylindrical or a cubic form, or the catalyst may assume the form of a rings, a tablet, a disc, or a pellet.

The catalyst essentially comprises a tungsten hydride that is grafted (covalently bonded) to alumina present in the support, generally by at least one single bond. The oxidation state of the tungsten hydride may have a value in a range from 2 to 6, and often from 4 to 6, which refers to the average oxidation state of tungsten atoms bonded to the alumina support. The tungsten hydride may furthermore be bonded to one or more atoms of hydrogen by single bonds (W—H) and optionally to one or more hydrocarbon residues, R, by single or multiple carbon-tungsten bonds. The number of hydrogen atoms bonded to an atom of tungsten depends on the oxidation state of tungsten, the number of single bonds between the tungsten atom and the support, and optionally the number of single or multiple bonds between the tungsten atom and a hydrocarbon residue, R. Thus, the number of hydrogen atoms bonded to a tungsten atom may be at least equal to 1 and at most equal to 5, and typically ranges from 1 to 4, and often from 1 to 3. Grafting or bonding of the tungsten hydride onto the solid support generally means that the tungsten atom is bonded by at least one single bond to alumina present in the support, and more particularly by at least one single bond (W—OAl) to at least one oxygen atom of the alumina. The number of single bonds between the tungsten atom and the alumina present in the support, in particular by a single bond (W—OAl), depends on the oxidation state of the tungsten and on the number of other bonds of the tungsten atom, and this number is generally 1, 2, or 3.

The tungsten atom of the tungsten hydride may optionally be bonded to one or more hydrocarbon residues, R, with one or more single, double, or triple carbon-tungsten bonds. The hydrocarbon residue(s), R, may be identical or different, saturated or unsaturated hydrocarbon residues, comprising, for example, generally from 1 to 20 and often from 1 to 10 carbon atoms. The hydrocarbon residues may optionally comprise silicon, as in the case of an organosilane residue. The hydrocarbon residues may be selected from (i) alkyl residues, such as linear or branched, aliphatic or alicyclic residues, for example alkyl, alkylidene or alkylidyne residues, having, for example, from 1 to 10 carbon atoms, (ii) aryl residues, having, for example, from 6 to 12 carbon atoms, and (iii) aralkyl, aralkylidene or aralkylidyne residues, for example, having from 7 to 14 carbon atoms.

The tungsten atom of the tungsten hydride, in addition to being bonded to alumina present in the catalyst support, may be bonded to the hydrocarbon residue, R, by one or more single, double, or triple carbon-tungsten bonds. The bond may be a single carbon-tungsten bond. In this case, the hydrocarbon residue, R, may be an alkyl residue, for example linear or branched, or an aryl residue, for example a phenyl residue, or an aralkylene residue, for example a benzyl residue, or a residue of the formula ($C_6H_5$—$CH_2$—$CH_2$—). An alkyl residue is generally taken to mean a monovalent aliphatic residue obtained from the removal of a hydrogen atom from a carbon atom in a molecule of an alkane, an alkene, or an alkyne. In the particular case of the hydrocarbon residue, R, an alkyl residue also includes a monovalent aliphatic residue obtained from the removal of a hydrogen atom from a carbon atom in a molecule of an organosilane. Alkyl residues therefore include, for example, methyl ($CH_3$—), ethyl ($C_2H_5$—), propyl ($C_2H_5$—$CH_2$—), neopentyl (($CH_3$)$_3$C—$CH_2$—), allyl ($CH_2$=CH—$CH_2$—), alkynyl (R—C≡C—) (e.g., ethynyl (CH≡C—)), and neosilyl ($CH_3$)$_3$Si—$CH_2$—) residues. The alkyl residue may be, for example, of the formula (R'—$CH_2$—) where R' represents a linear or branched alkyl residue.

A double carbon-tungsten bond may also bond the tungsten hydride to the hydrocarbon residue, R. In this case, the hydrocarbon residue, R, may be an alkylidene residue, which may be linear or branched, or an aralkylidene residue. An alkylidene residue is generally a divalent aliphatic residue originating from the removal of two hydrogen atoms from the same carbon atom in the molecule of an alkane, or an alkene, or an alkyne, or even of an organosilane. Alkylidene residues therefore include, for example, methylidene ($CH_2$=), ethylidene ($CH_3$CH=), propylidene ($C_2H_5$—CH=), neopentylidene (($CH_3$)$_3$C—CH=), or allylidene ($CH_2$=CH—CH=) residue. The alkylidene residue may be, for example, of the formula (R'—CH=) where R' represents a linear or branched alkyl residue. An aralkylidene residue is generally taken to mean a divalent aliphatic residue originating from the removal of two hydrogen atoms from the same carbon in an alkyl, alkenyl or alkynyl residue bonded to an aromatic group.

A triple carbon-tungsten bond may also bond the tungsten hydride to the hydrocarbon residue, R. In this case, the hydrocarbon residue, R, may be an alkylidyne residue, which may be linear or branched, or an aralkylidyne residue. An alkylidyne residue is generally a trivalent aliphatic residue originating from the removal of three hydrogen atoms from the same carbon atom in the molecule of alkane, or an alkene, or an alkyne, or even of an organosilane, for example an ethylidyne ($CH_3$—C≡), propylidyne ($C_2H_5$—C≡), neopentylidyne ($CH_3$)$_3$C—C≡) or allylidyne ($CH_2$=CH—C≡) residue. The alkylidyne residue may be, for example, of the formula (R'—C≡), where R' represents a linear or branched alkyl residue. An aralkylidyne residue is generally a trivalent aliphatic residue originating from the removal of three atoms of hydrogen from the same carbon of an alkyl, alkenyl, or alkynyl residue bonded to an aromatic group.

Representative hydrocarbon residues, R, are selected from methyl, ethyl, n-propyl, isopropyl, n-butyl, isobutyl, neopentyl, allyl, neopentylidene, allylidene, neopentylidyne, and neosilyl.

The tungsten atom of the tungsten hydride that is grafted (bonded) to alumina present in the catalyst support may be complexed with one or more hydrocarbon ligands, for example aromatic or carbonyl ligands. A particular type of bonding of the tungsten hydride to alumina through a W—OAl linkage may be represented as follows:

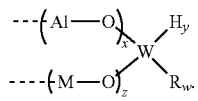

The tungsten hydride bonded to alumina of the support may therefore be represented by the above formula, wherein W, Al, O and H respectively represent atoms of tungsten, aluminum, oxygen and hydrogen, and M represents an atom of one or more elements of another oxide present in the support, as defined previously. R represents a hydrocarbon residue, as defined previously, and w, x, y, and z are integers, the sum of which (w+x+y+z) equals 2 to 6 (i.e., the oxidation state of the tungsten), wherein x=1 to 3, y=1 to 5, w=0 to 4 and z=0 to 2. The value of z is 0, for example, when the tungsten hydride is not bound, through an oxygen linkage, to a metal other than aluminum in the catalyst support. This condition occurs, for example, when the support comprises all or substantially all alumina. In the above formula, the —(Al—O) and -(M-O) bonds represent one or more single or multiple bonds, respectively, bonding the aluminum atom and the metal atom M to one of the atomic constituents of the support comprising alumina, and in particular to one of the oxygen atom constituents of this support.

Under infrared spectroscopy, the catalysts comprising a tungsten hydride, as described herein, generally exhibit one or more absorption bands which are characteristic of the (W—H) bond, the frequency of which bands may vary depending on the coordination sphere of the tungsten and particularly on the number of bonds of the tungsten with the support, with hydrocarbon residues R, and with other hydrogen atoms. Accordingly, at least two absorption bands have been found at 1903 cm$^{-1}$ and 1804 cm$^{-1}$, being characteristic of the (W—H) bond and in particular in the environment of the (W—OAl) bond, bonding the same tungsten atom of the tungsten hydride to an oxygen atom, which is in turn bonded to an aluminum atom of an α-alumina. By way of comparison, tungsten hydride grafted (bonded) under the same conditions onto a silica support generally exhibits under infrared spectroscopy at least one absorption band at 1940 cm$^{-1}$ or 1960 cm$^{-1}$, being characteristic of the (W—H) bond and in particular in the environment of the (W—OSi) bond, bonding the same tungsten atom of the tungsten hydride to an oxygen atom, which is in turn bonded to a silicon atom of the silica support.

The presence of a (W—H) bond of a tungsten hydride, which is bonded to alumina in the catalyst support, may also be detected using proton nuclear magnetic resonance (solid 1H-NMR) at 500 MHz, where the value of the tungsten hydride chemical shift $\delta_{W-H}$ is typically found at a value of about 10.6 parts per million (ppm) (e.g., in the range from about 10.3-10.9 ppm).

In addition to a tungsten hydride, the catalyst may further comprise an aluminum hydride, for example at the surface of the support and/or in the vicinity of the grafted tungsten hydride. Without being bound by theory, it is believed that an aluminum hydride can be formed by opening of an aluminoxane bridge (of the formula Al—O—Al), which may be present at the surface of the support, and by reaction of the opened aluminoxane bridge and a hydrogen atom of a grafted tungsten hydride. A simple method for detecting the presence of aluminum hydride, in addition to tungsten hydride, in the catalyst involves performing a deuteration reaction of the catalyst. According to a particular method, the catalyst is subjected to a deuterium atmosphere under an absolute pressure of 66.7 kPa (10 psi) and a temperature generally from 25° C. (77° F.) to 80° C. (176° F.), and often about 60° C. (140° F.), for a period of about 15 minutes. Selective deuteration under these conditions replaces hydrogen atoms of the (W—H) bond with deuterium atoms, thereby forming (W-D) bonds which, under IR spectroscopy, have absorption bands at 1293 cm$^{-1}$ and 1393 cm$^{-1}$. Selective deuteration leaves the hydrogen atoms in the (Al—H) bonds unchanged, and these bonds may be identified under IR spectroscopy by an absorption band at 1914 cm$^{-1}$.

The solid supported catalyst, comprising a tungsten hydride grafted (bonded) to alumina present in the support, may be prepared by a method comprising dispersion and grafting of an organometallic tungsten precursor (Pr) onto a support comprising alumina. The tungsten in the precursor may be either bonded or otherwise complexed to at least one hydrocarbon ligand, so as to form a hydrocarbon compound or hydrocarbon complex, respectively, of tungsten grafted onto the support. Then, hydrogenolysis of the grafted hydrocarbon compound or hydrocarbon complex of tungsten, resulting from the previous dispersion and grafting, forms tungsten hydride grafted onto alumina of the support.

The organometallic tungsten precursor, Pr, may comprise a tungsten atom bonded to one or more hydrocarbon ligands. The tungsten atom may be bonded to a carbon of the hydrocarbon ligand by single, double or triple (carbon-tungsten) bonds. The hydrocarbon ligands may be identical or different, saturated or unsaturated hydrocarbon residues, for example aliphatic or alicyclic residues, generally having from 1 to 20 carbon atoms and often from about 1 to 10 carbon atoms. The hydrocarbon ligands may be selected from the hydrocarbon residues, R, described previously. The number of hydrocarbon ligands bonded to the tungsten atom depends on the oxidation state of tungsten in the precursor Pr and may be at most equal to this oxidation state. The number of hydrocarbon ligands may therefore be from 1 to 6, typically from 2 to 6, and often from 4 to 6.

The precursor, Pr, may also comprise a tungsten atom complexed to one or more hydrocarbon ligands, the oxidation state of the tungsten being in this case equal to zero. The hydrocarbon ligand may be selected from among aromatic ligands or carbonyl ligands. The precursor Pr may accordingly be selected from among bis-arene tungsten and hexacarbonyl tungsten.

Prior to dispersion and grafting of the organometallic precursor, the support comprising alumina may be subjected to calcination and/or dehydroxylation. Calcination of the support may be performed to oxidize any carbon optionally present in the support and thereby eliminate it as carbon dioxide. Calcination may involve subjecting the support to an oxidizing heat treatment, for example under a stream of dry air, at a temperature below the sintering temperature of the support. Suitable temperatures are generally from 100° C. (212° F.) to 1000° C. (1832° F.), and typically from 200° C. (392° F.) to 800° C. (1472° F.), for a duration sufficient to eliminate the carbon dioxide. The duration may range from 0.1 to 48 hours, and the calcination may be conducted at atmospheric pressure or otherwise under elevated pressure or subatmospheric pressure.

The support may also be subjected to dehydroxylation prior to dispersion and grafting of the organometallic precursor, Pr. Dehydroxylation may be performed to optionally eliminate residual water from the support, as well as a proportion of the hydroxyl groups. A residual quantity of hydroxyl groups is left behind, generally at the surface of the support, and optionally aluminoxane bridges (of the formula Al—O—Al) are formed. Dehydroxylation may be performed by subjecting the support to heat treatment under a stream of inert gas, for example under a stream of nitrogen, argon or helium, under a pressure which is preferably below atmospheric pressure, for example under an absolute pressure of from $10^{-4}$ Pa ($1.5 \times 10^{-8}$ psia) to $10^2$ kPa (14.5 psia), preferably from $10^{-2}$ Pa ($1.5 \times 10^{-6}$ psia) to 50 kPa (7.3 psia), at a temperature below the sintering temperature of the support, for example at a temperature generally from 100° C. (212° F.) to 1000° C. (1832° F.), and typically from 200° C. (392° F.) to 800° C. (1472° F.), and for a duration sufficient to leave behind an appropriate residual quantity of hydroxyl groups and/or aluminoxane bridges in the support. The duration may range from 0.1 to 48 hours. Also, the dehydroxylation step may advantageously be performed after the calcination step.

The dispersion and grafting or bonding of the organometallic precursor, Pr, may be performed by sublimation, by impregnation with the assistance of a solvent, or by dry mixing. In the case of sublimation, the precursor, Pr, which is generally in the solid state under normal conditions, is heated normally under subatmospheric pressure and at a temperature causing its sublimation and migration in the gaseous state onto the support. Sublimation may be performed at a temperature of from −30° C. (−22° F.) to 200° C. (392° F.), and at an absolute pressure from $10^{-4}$ Pa ($1.5 \times 10^{-8}$ psia) to 10 kPa (1.45 psia). Grafting of the precursor, Pr, onto the support may be monitored by IR spectroscopy. Any excess precursor Pr which has not grafted (bonded) onto the support may be removed by inverse sublimation.

The dispersion and grafting may also be performed by impregnation with the assistance of a solvent. In this case, the precursor, Pr, may be dissolved in a polar or non-polar organic solvent, for example pentane or ethyl ether. Impregnation may be performed by contacting the support comprising alumina with the impregnation solution of the precursor, Pr. Impregnation may be performed at a temperature of from −80° C. (−122° F.) to 200° C. (392° F.), under an inert atmosphere, for example an atmosphere of nitrogen, argon and/or helium, and preferably with stirring. In this manner, a suspension of a hydrocarbon compound or a complex of tungsten grafted onto the support is obtained. Any excess precursor Pr which has not grafted (bonded) onto the support may be removed by washing with an organic solvent, which may be identical to or different from that used during impregnation.

The dispersion and grafting may also be performed by dry mixing, including mechanical dry mixing in the absence of liquid or liquid solvent. In this case, the precursor, Pr, which is generally in the solid state under normal conditions, is mixed with the support comprising alumina in the absence of liquid or liquid solvent. Mechanical stirring under an inert atmosphere, for example an atmosphere of nitrogen, argon and/or helium, is used to form a mixture of two solids. During or after the dry mixing, heat and/or subatmospheric pressure may be used to cause migration of the precursor, Pr, and its reaction with and covalent bonding to the support. Any precursor that has not been grafted (bonded) onto the support may be removed by inverse sublimation or washing with organic solvent.

Production of the catalyst may further comprise hydrogenolysis, or reaction of the hydrocarbon compound, or alternatively the hydrocarbon complex, of tungsten grafted onto the support, as prepared in the manner described previously. The reaction is carried out to form a tungsten hydride grafted (bonded) onto the support. Hydrogenolysis is generally understood to mean a reaction involving cleavage of a molecule that accompanies bonding of hydrogen onto the two cleaved ends. Cleavage in this case occurs between the tungsten atom grafted onto the support and the carbon atom of a hydrocarbon ligand that is bonded to or otherwise complexed with the tungsten atom. Hydrogenolysis may be performed with the assistance of hydrogen or a reducing agent that is capable of converting the grafted hydrocarbon compound or hydrocarbon complex of tungsten into grafted tungsten hydride. Hydrogenolysis may be performed by contacting the grafted hydrocarbon compound or hydrocarbon complex of tungsten with the hydrogen or reducing agent. It may be performed under an atmosphere of hydrogen or an inert atmosphere when a reducing agent is used, using an absolute pressure of from $10^{-2}$ Pa ($1.5 \times 10^{-6}$ psia) to 10 MPa (145 psia), at a temperature of from 20° C. (68° F.) to 500° C. (932° F.) for a period of from 0.1 to 48 hours.

Overall aspects of the invention are directed to processes that exploit the unexpected findings found to be associated with the use of a particular catalyst system, known to be effective in olefin metathesis, for the conversion of acyclic symmetrical olefins to olefin products of higher and lower carbon numbers. More specifically, operating under process conditions expected to promote olefin metathesis, in the presence of a catalyst comprising a tungsten hydride bonded to alumina present in the catalyst support, provides important commercial advantages in terms of conversion of an acyclic symmetrical olefin (e.g., butene-2) with good selectivity to desired product(s) (e.g., propylene) having a different carbon number. Those having skill in the art, with the knowledge gained from the present disclosure, will recognize that various changes can be made in the above catalysts and processes using the catalysts, without departing from the scope of the present disclosure.

The following examples are representative of the present invention and its associated advantages and are not to be construed as limiting the scope of the invention as set forth in the appended claims.

EXAMPLE 1

Conversion of Butene-2 to Propylene and Other Products with W—H/$Al_2O_3$ Catalysts A solid catalyst comprising a tungsten hydride grafted (bonded) to alumina was prepared as described in Example 3 of US 2007/0129584. The alumina used in this case was Aeroxide® Alu C (Evonik Degussa GmbH, Essen, Germany), having a surface area of 125 $m^2$/g. The tungsten content of the catalyst was 3.0 wt-%, based on the total catalyst weight. The catalyst was evaluated, according to a microreactor-scale experimental protocol, for the production of propylene and other products from a pure butene-2 feedstock under conditions generally favorable for olefin metathesis. In particular, butene-2 was passed over a 150 mg sample loading of the catalyst at a temperature of 150° C. (302° F.) and a flow rate of about 7.6 Nml/min, corresponding to a weight hourly space velocity (WHSV) of about 7 hr$^{-1}$. These conditions and 1 barg (15 psig) were maintained over a testing duration of about 45 hours.

The reactor effluent composition was analyzed periodically by gas chromatography to determine both (i) the conversion level (per pass) of butene-2 and (ii) the turnover number, defined as the total moles of butene-2 converted per mole of tungsten metal in the catalyst, as a function of time on stream. These results are shown in FIG. 1. The analytical results of the reactor effluent were also used to calculate product selectivities, based on the total percentage of converted butene-2 that resulted in the formation of propylene (propylene selectivity), $C_5$ olefins, and $C_6$ olefins. These results are shown in FIG. 2.

The data illustrate that butene-2 is effectively converted to propylene and other products, including a significant amount of pentene, under conditions and in the presence of a catalyst that are expected to lead to degenerative olefin metathesis, without the appreciable formation of products having different carbon numbers.

The invention claimed is:

1. A process for producing olefins, the process comprising: contacting a hydrocarbon feedstock with a catalyst comprising a solid support and a tungsten hydride bonded to alumina present in the support, wherein the hydrocarbon feedstock consists essentially of an acyclic symmetrical olefin, without any ethylene, to produce first and second olefin products, respectively, having a lower carbon number and a higher carbon number relative to the acyclic symmetrical olefin, wherein-the acyclic symmetrical olefin is converted to the first olefin having a lower carbon number relative to the acyclic symmetrical olefin with a selectivity of at least 45% by weight.

2. The process of claim 1, wherein the catalyst comprises tungsten in an amount from about 1% to about 10% by weight.

3. The process of claim 1, wherein the support comprises alumina in an amount of at least about 95% by weight.

4. The process of claim 1, wherein the support has a BET surface area from about 100 m$^2$/g to about 450 m$^2$/g, wherein the BET surface area measurement is based on nitrogen adsorption.

5. The process of claim 1, wherein the average oxidation state of tungsten in the tungsten hydride is from 4 to 6.

6. The process of claim 1, wherein the acyclic symmetrical olefin is present in an amount of at least 80% by weight of the hydrocarbon feedstock.

7. The process of claim 1, wherein the acyclic symmetrical olefin is present in an amount of at least 85% by weight of the hydrocarbon feedstock.

8. The process of claim 1, wherein the acyclic symmetrical olefin is converted at a per pass conversion of at least about 15% by weight.

9. The process of claim 8, wherein the acyclic symmetrical olefin is converted to the second olefin product with a selectivity of at least about 30% by weight.

10. The process of claim 8, wherein the acyclic symmetrical olefin is converted at a per pass conversion from about 15% to about 50% by weight.

11. The process of claim 1, wherein the hydrocarbon feedstock is contacted with the catalyst at a temperature from about 75° C. (167° F.) to about 250° C. (482° F.), an absolute pressure from about 0.5 bar (7.3 psi) to about 35 bar (508 psi), and a weight hourly space velocity from about 1 hr$^{-1}$ to about 100 hr$^{-1}$.

12. The process of claim 1, wherein the acyclic symmetrical olefin is butene-2, the first olefin product is propylene, and the second olefin product is pentene.

13. The process of claim 12, further comprising recovering the propylene with a purity of at least about 99.5% by volume.

14. The process of claim 12, wherein at least a portion of the butylene is obtained from an oxygenate to olefins conversion process or a fluid catalytic cracking process.

15. The process of claim 12, wherein the butene-2 is converted at a per pass conversion of at least about 15% by weight.

16. The process of claim 15, wherein the per pass conversion is from about 15% to about 50% by weight.

17. The process of claim 12, wherein the butene-2 is converted to pentene with a selectivity of at least about 30% by weight.

18. A process for producing propylene, the process comprising contacting a hydrocarbon feedstock comprising butene-2, without any ethylene, in an amount of at least 80% by weight with a catalyst comprising a solid support and a tungsten hydride bonded to alumina present in the support, wherein a per pass conversion of butene-2 is from about 15% to about 50% by weight and wherein the butene-2 is converted to propylene with a selectivity of at least about 45% by weight.

19. A process for producing olefins, the process comprising:
contacting a hydrocarbon feedstock with a catalyst comprising a solid support and a tungsten hydride bonded to alumina present in the support, wherein the hydrocarbon feedstock consists essentially of an acyclic symmetrical olefin, without any ethylene, of at least 80% by weight of total olefins in the hydrocarbon feedstock and wherein olefins having the same carbon number as the acyclic symmetrical olefin are present in an amount of from about 95% to about 100% by weight of total olefins in the hydrocarbon feedstock to produce first and second olefin products, respectively, having a lower carbon number and a higher carbon number relative to the acyclic symmetrical olefin, wherein the acyclic symmetrical olefin is converted to the first olefin having a lower carbon number relative to the acyclic symmetrical olefin with a selectivity of at least 45% by weight.

20. The process of claim 19 wherein the stream comprising the acyclic symmetric olefin is subjected to isomerization upstream of said contact of said hydrocarbon feedstock with said catalyst.

* * * * *